US012809042B2

(12) United States Patent
Tashenov

(10) Patent No.: US 12,809,042 B2
(45) Date of Patent: Nov. 24, 2026

(54) DEVICE AND METHOD TO INTRAOPERATIVELY MEASURE RADIOACTIVITY OF RADIOEMBOLIZATION AGENT

(71) Applicant: VARIAN MEDICAL SYSTEMS, INC., Palo Alto, CA (US)

(72) Inventor: Stanislav Tashenov, Heroldsbach (DE)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 106 days.

(21) Appl. No.: 18/852,567

(22) PCT Filed: May 15, 2023

(86) PCT No.: PCT/US2023/022255

§ 371 (c)(1),
(2) Date: Sep. 30, 2024

(87) PCT Pub. No.: WO2023/224918

PCT Pub. Date: Nov. 23, 2023

(65) Prior Publication Data

US 2025/0216560 A1 Jul. 3, 2025

Related U.S. Application Data

(60) Provisional application No. 63/342,469, filed on May 16, 2022.

(51) Int. Cl.

| | |
|---|---|
| ***G01T 1/02*** | (2006.01) |
| ***A61K 51/12*** | (2006.01) |
| ***A61N 5/10*** | (2006.01) |
| ***G01T 1/00*** | (2006.01) |

(52) U.S. Cl.

CPC .......... *G01T 1/023* (2013.01); *A61K 51/1251* (2013.01); *A61N 5/1002* (2013.01); *G01T 1/003* (2013.01); *A61K 2121/00* (2013.01)

(58) Field of Classification Search

CPC ...................................................... G01T 1/023

See application file for complete search history.

(56) References Cited

U.S. PATENT DOCUMENTS

| | | | | |
|---|---|---|---|---|
| 2017/0360968 A1* | 12/2017 | Boyd | ................. | A61K 51/1244 |
| 2021/0369946 A1* | 12/2021 | Akerele-Ale | ..... | A61M 25/0071 |

FOREIGN PATENT DOCUMENTS

| | | | | |
|---|---|---|---|---|
| ES | 2965833 T3 * | 4/2024 | ........ | A61M 5/31596 |
| WO | WO-2025038072 A1 * | 2/2025 | ........... | A61N 5/1048 |

* cited by examiner

*Primary Examiner* — Edwin C Gunberg

(74) *Attorney, Agent, or Firm* — Morgan, Lewis & Bockius LLP; Manita Rawat

(57) ABSTRACT

A device to measure radioactivity of a radioembolization material including a container 110 to receive the radioembolization material; and a dosimeter 140 that measures the radioactivity of the radioembolization material in the container while the radioembolization material is being administered to a patient.

20 Claims, 4 Drawing Sheets

DEVICE AND METHOD TO INTRAOPERATIVELY MEASURE RADIOACTIVITY OF RADIOEMBOLIZATION AGENT

CROSS REFERENCE TO RELATED APPLICATIONS

This application is a National Stage Application, filed under 35 U.S.C. 371, of International Patent Application No. PCT/US2023/022255, filed on May 15, 2023, which claims the benefit of U.S. Provisional Patent Application No. 63/342,469, filed May 16, 2022, each of which is hereby incorporated by reference in its entirety for all purposes as if fully set forth herein.

TECHNICAL FIELD

This disclosure relates to selective internal radiation therapy (SIRT) dosimetry. More specifically, the disclosure relates to devices and methods that measure radioactivity of a radioembolization agent prior to being administered to a patient.

BACKGROUND

In existing methods of selective internal radiation therapy (SIRT) a combination of angiography (C-arm) and nuclear imaging, is typically used. The nuclear imaging in such methods is often in the form of scintigraphy or single photon emission computed tomography (SPECT). SIRT procedures include embolization of tumor-feeding blood vessels with radioactive microspheres with the help of C-arm imaging. The microspheres serve a dual purpose; (i) they close or restrict the micro-blood vessels that feed the tumor to deprive the tumor of the supply of oxygen and nutrients, and (ii) at the same time, the microspheres, including a radioisotope that emits electrons in the MeV energy range, are used to deliver high doses of radiation to the tumor. This selective delivery of high doses of radiation to kill cancerous lesions spares healthy surrounding tissue. Liver tumors are often treated with SIRT.

SUMMARY

Conventionally, several techniques can be used to deliver microspheres to the tissue of interest. One technique is delivering the microspheres via a hepatic artery that delivers the microspheres to the whole liver or organ of interest. In this technique, branching of this artery introduces a risk of unintended embolization of other blood vessels and organs. Alternatively, microspheres can be delivered using a distal approach. In this approach, the administering catheter is positioned closer to the lesion, such that blood flow from this position covers the whole lesion and has no or minimal coverage of the heathy liver tissue. With this technique, the risk of unintended delivery of microspheres is reduced. This technique allows more selective embolization, in particular lobectomy and radiation segmentectomy. In these cases, the amount of delivered microspheres needs to be divided into several portions, which makes this procedure more complex. Currently, the embolization microspheres are mixed, and the amount of contrast medium and the fractions delivered to each affected distal vessel are approximated by a technician. Therefore, there is a need to quantitatively deliver given proportions of microspheres into specific organ sections.

It is possible to perform SIRT evaluation and SIRT treatment procedures in one session. SIRT evaluation can be used to gather information on arterials structures and blood flow at the tissue of interest and anticipate microbead accumulation in parenchyma and/or tumor tissue in the organ. For the SIRT treatment the total amount of the microspheres delivered to the tissue of interest (radiation activity) needs to be calculated and prepared based on the patient's anatomy. This considers the size (mass) of the patient's liver or organ of interest and the hepatopulmonary shunting fraction. The hepatopulmonary shunting fraction can only be obtained during SIRT evaluation. Therefore, at the start of the combined evaluation and treatment procedure, the total needed radiation activity has not yet been determined. However, the vials containing the microspheres are provided to treatment facilities with a predetermined radiation activity at the intended date of the procedure. In some existing treatment methods, without any adjustment, a technician delivers the entire contents of the vial into the patient. Thus, it is not possible to change the total injected activity during the treatment procedure in existing treatments using traditional methods and devices. Also, once determined, the desired amount of radiation activity for a given patient and procedure is prepared by nuclear physicists (lab personnel) typically at a location remote from the treatment facility. This process requires preparation and/or delivery time. Thus, existing treatment methods and devices do not allow for the quantitative measuring and delivery of customized radiation doses without stopping or interrupting the SIRT treatment procedure.

The disclosed embodiments have been found to allow a technician to provide any amount of radioembolization material, both for evaluation and for therapy. The technician can calculate the needed amount of the radioembolization material during the procedure (after the hepatopulmonary shunting fraction was determined) and continue with the embolization (therapy phase) without interrupting the procedure or waiting for the nuclear lab to prepare vials with the needed amount.

Additionally, the methods and devices of the present disclosure allow a technician to deliver predetermined, desired and/or calculated radioactive doses into several distal vessels quantitatively rather than qualitatively.

According to an embodiment, a device to measure radioactivity of a radioembolization material includes a container to receive the radioembolization material; and a dosimeter that measures the radioactivity of the radioembolization material in the container while the radioembolization material is being administered to a patient.

According to another embodiment, a device to measure radioactivity of a radioembolization material includes a dosimeter positioned adjacent to a conduit during a radioembolization procedure, the dosimeter configured to measure the radioactivity of the radioembolization material as the radioembolization material moves through the conduit; and a flow meter that measures a flow velocity of the radioembolization material as the radioembolization material moves through the conduit.

According to another embodiment, a method to measure radioactivity of a radioembolization material administered into a patient's vasculature includes measuring an initial radioactivity and a subsequent radioactivity of the radioembolization material in a vial using a dosimeter during a radioembolization treatment; and calculating a difference between an initial radioactivity of the radioembolization material in the vial prior to administration of the radioembolization material into the patient's vasculature and a subsequent radioactivity of the radioembolization material before ceasing administration of the radioembolization material into the patient's vasculature.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like components and further wherein.

DETAILED DESCRIPTION

Figure 1:
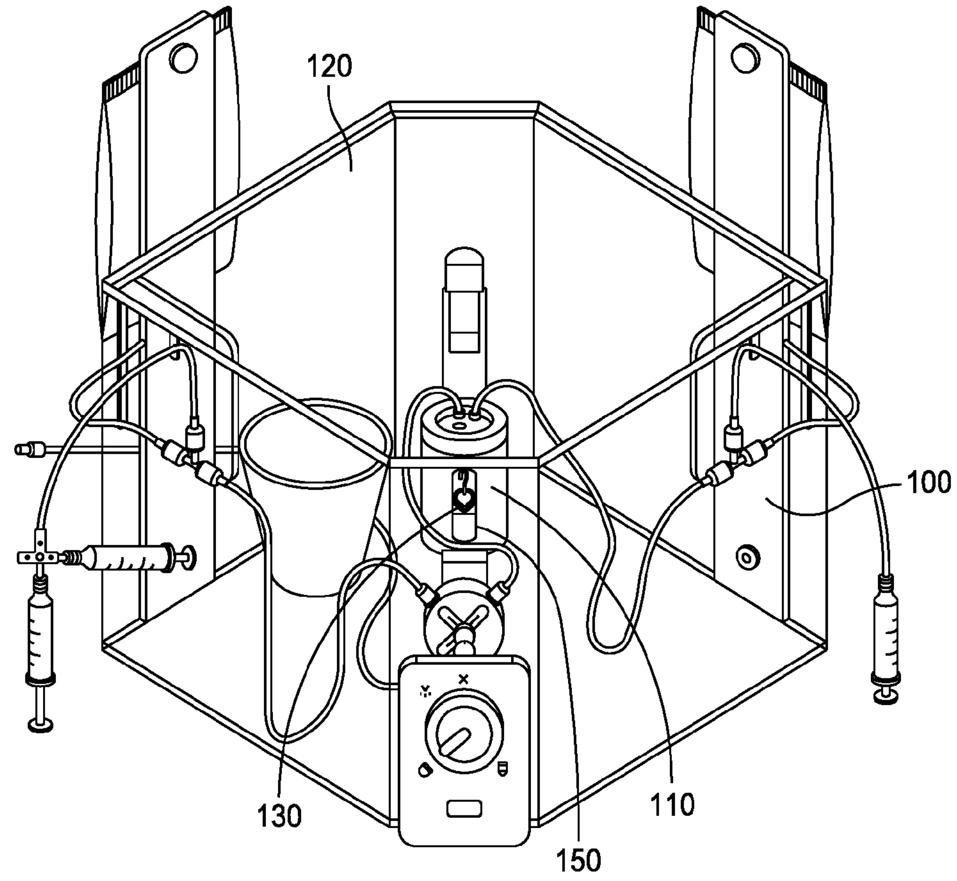
FIG. 1 is an illustration of an embolization box according an embodiment of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments.

Figure 2:
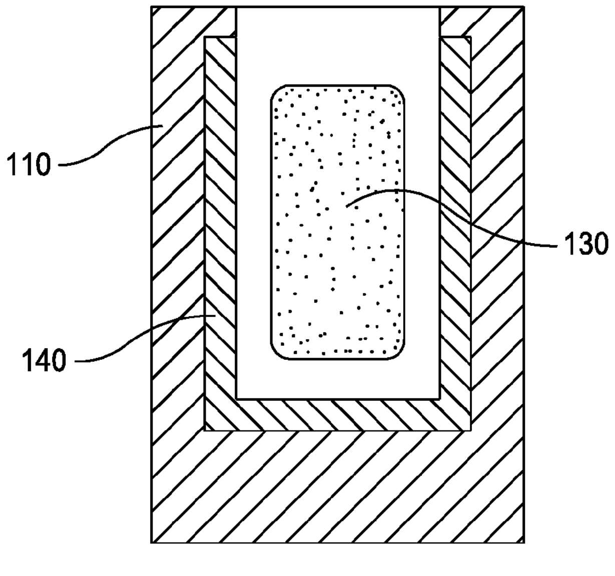
FIG. 2 is a side cross-sectional illustration of a container.

FIGS. 1 and 2 are used to describe an embodiment of the current disclosure that includes features to quantitatively measure radioactivity of a radioembolization agent injected into a patient's vasculature. FIG. 1 is an illustration of an embolization box 100. As shown, the embolization box 100 includes a space inside to house a container 110 that can contain a vial 130 of radioembolization material. Yttrium-90 (Y-90), Technetium-99 m (Tc-m 99), Holmium-166, or any other suitable isotope can be used. Holmium-166 also emits gamma rays with an energy of 81 keV.

As shown, the embolization box 100 can include a lid 120 or a door that can be opened and closed to access the inner space. The container 110 can be housed inside the embolization box 100 and include a space to hold the vial 130. As shown in FIG. 2, the container 110 can also include a dosimeter 140 (gamma-ray detector) that measures ionizing radiation of radioisotopes inside the vial 130. A display 150 that displays the measured radiation value can be included with the embolization box 100. The display 150 can be coupled to the dosimeter via a suitable cable and can be positioned externally to the embolization box 100 so as to not be obscured by the catheters, conduits and other delivery elements. Alternatively, the dosimeter 140 can be connected to a display of an angiography unit. In this case, the activity information (which corresponds to the dose) can be conveniently viewed by a technician on a larger display, which is also displaying real-time fluoroscopy scene. As fluoroscopy and activity flow need to be viewed simultaneously, it is advantageous to display them on the same screen. The embolization box 100 can be made of acrylic (PMMA) or any other suitable transparent material and can block a significant portion of the radiation.

The dosimeter 140 can include a scintillator such as a photomultiplier, detectors and/or other suitable structure used to measure the radioactivity of the radioembolization material in the vial 130. As will be further described below, the scintillator can be arranged in a suitable manner to actively and/or continuously monitor and measure the radioactivity of the radioembolization material. The dosimeter 140 can be used, for example, to determine an initial radioactivity of the radioembolization material prior to a start of a radioembolization procedure and a second radioactivity after some portion of the radioembolization material has been delivered to the patient during the procedure. In this manner, a radioactivity dose that has been delivered during the procedure can be quantitatively determined.

During an example procedure, the vial 130 can be stored in the container 110. The container 110 incorporates the dosimeter 140 that periodically and/or continuously measures the total gamma-ray activity emanating from the vial 130. The container 110 allows radioactivity measurement of the radioembolization material such as Yttrium-90-based microspheres and/or Holmium-166-based microspheres inside of the vial 130. The container 110 can also be used for other radioembolization materials such as Techniceum-99 m-based embolization particles, which can be used during SIRT evaluation procedures.

The dosimeter 140 can be coupled to a display 150 and/or to other computing devices, treatment devices, embolization devices, displays, user interfaces, and the like. The radioactivity of the vial 130 can be displayed on the display 150. Alternatively, the radioactivity of the vial 130 can be displayed on a display that is a component of the C-arm imaging system or both. A difference between the initial radioactivity of the material in the vial 130 and the current radioactivity can be also displayed. This difference will quantify the radioactivity delivered into the patient' vasculature. By measuring the radioactivity periodically or continuously, the rate of delivery of the radioembolization material can be also displayed. In other examples, the measured radioactivity, rate of delivery of the radioembolization material, and/or other information measured by the dosimeter 140 can be provided to a computing device, database, treatment device or other system for display, storage, and/or further use.

Figure 3:
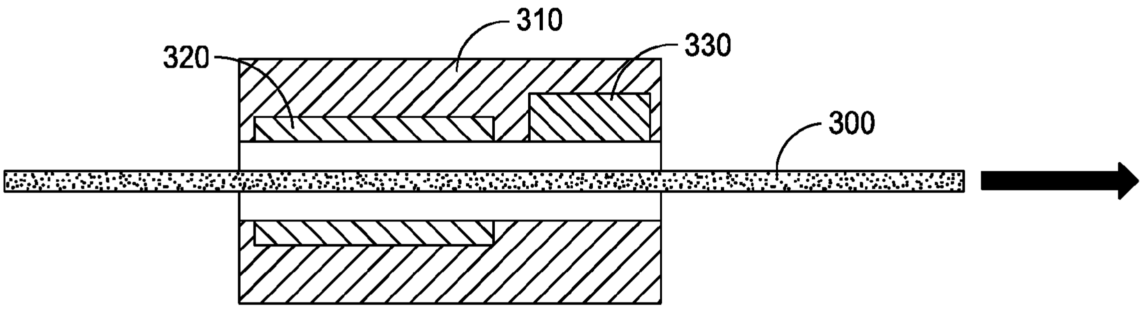
FIG. 3 is a side cross-sectional illustration showing a catheter and an activity flow meter according to another embodiment of the present disclosure.

FIG. 3 is a diagram of another embodiment that includes features to quantitatively measure radioactivity of a radioembolization agent delivered into patient's vasculature. FIG. 3 shows that a catheter 300 that delivers the radioembolization material can be pass through an activity flow meter 310. The activity flow meter 310 can be positioned, for example, downstream of a vial of radioembolization material. The activity flow meter 310 can be positioned over a conduit that fluidly connects the vial to a device that administers the radioembolization material to the patient such as a needle, catheter, or the like. While a catheter 300 is shown in FIG. 3, the activity flow meter 310 can also be positioned over a tube, conduit, or other structure through which the radioembolization material travels before delivery to the patient.

As shown in one example, the activity flow meter 310 can be attached to the catheter 300 and used to monitor the activity of embolization particles which are being delivered to the patient. As shown, the activity flow meter 300 can include a dosimeter 320 and a flow meter 330. The dosimeter 320 (gamma-ray detector) measures the total radioactivity within the section of the catheter 300 passing through the dosimeter 320. The dosimeter 320 can include one or more scintillators, photomultipliers, detectors, and other device to measure the radioactivity of the radioembolization material.

The flow meter 330 measures the speed of the embolization material moving through the catheter 300. In the example shown, the flow meter 330 is positioned downstream of the dosimeter 320. In other examples, the flow meter 330 can be positioned at other locations such as upstream of the dosimeter 320. The flow meter 330 is configured to measure a flow rate of the radioembolization material as it passes through the activity flow meter 310. In one example, the flow meter 330 is an optical flow meter. In other examples, other flow meters can be used such as ultrasound flow meters, electromagnetic flow meters, and others. The radioactivity and the flow rate of the radioembolization materials that passes through the activity flow meter can be measured periodically or continuously. This information can be transferred, stored, and/or used to determine radioactivity and radioactive doses being delivered to a patient. Using the measured activity and the velocity of the radioembolization material, one can calculate the rate with which the radioactivity is being delivered to the patient, for example.

Similar to the container 110 previously described, the activity flow meter 310 can be coupled to a display, computing device, medical treatment device, database, or other user interface. The rate of the radioactivity injection and the total injected radioactivity can be displayed for the technician either on the activity flow meter 310, the imaging system, separate display or any other convenient location. In other examples, the radioactivity information that is measured by the activity flow meter 310 can be provided to other computing devices, medical equipment, databases, and the like for display, storage, and/or further use.

As previously discussed, the dosimeters of the present disclosure can be used to determine a radioactive dose that is delivered to a patient during a radioembolization procedure. The dosimeters of the present disclosure also have other uses that provide advantages and improvements over existing methods and equipment. It can be difficult, for example, to accurately determine an age of a prepared radioembolization material. In addition, there may be a risk associated with delivering the incorrect radioembolization material to a patient. The dosimeters of the present disclosure can be used to improve present methods by allowing the accurate determination of an age of a radioembolization agent. Such determination can then be used, for example, to verify that the correct or desired radioembolization agent is delivered to the patient during treatment.

The dosimeters of the present disclosure can be used, for example, to measure an age of a radioembolization material if such material includes multiple sources of radioactivity. For example, it can be possible to detect and measure an age of a radioembolization material that includes Y-90 radioembolization material and another suitable radioembolization material which emits direct gamma-rays (e.g. Cu-67). If such additional material or microbeads emit direct gamma rays (e.g. Ho-166 emits 80 keV), it is possible to detect and count them due to their higher activity and measure the activity of the direct gamma ray emission. If the gamma ray emitter and Y-90 have different decay rates (i.e. half-life times), which will be the case with a Y-90 and direct gamma-ray microbeads mixture, it will be possible to determine the age of the mixed radioembolization material as described below. In other embodiments, other isotypes may be used, such as but not limited to Technetium-99 m (Tc-m 99) and Holmium-166.

If the initial activities of the mixed emitters are fixed by production, a measurement of their activity ratio can be used to determine the age of the mixture. This can be used to reduce human error and avoid using the wrong vial for a patient. By knowing the age of the mixture, and by measuring the injected activity, the total radiodensity of the injected microbeads can be determined in Hounsfield Units (HU). A DynaCT will detect only dense regions of the microbeads, it can measure the total radiodensity in the dense regions, and therefore the radioactivity. Less dense regions will be undetected in the DynaCT. The dosimeter will provide the total value of the injected radioactivity. By understanding the total injected radioactivity to the liver tissue (or organ/tissue of interest), it is possible to determine the residual dose to healthy liver tissue.

In the embodiments described above, the radioactivity measurement can be done using either (i) a scintillating detector (highest efficiency) or (ii) a semiconductor detector or ionization chamber. Bremsstrachlung radiation, electromagnetic radiation produced by the deceleration of a charged particle when deflected by another charged particle, can also be measured. For example, there is an opportunity to increase the bremsstrahlung rate by including an inner coating on the catheter including a heavy metal (e.g. Bi, Pt, Au, Ta) or other suitable bremsstrahlung producing material. The metal coating can be thin enough so as to not shield or overly attenuate any gamma rays produced directly by isotopes present in the mixture.

In aspects of the disclosure, FIGS. 4, 5, and 7 are used to show scintillator configurations. Such configurations can be used, for example, with the container 110 and/or the activity flow meter 310 previously described. In scintillation detectors the material of the detector is excited to luminescence (emission of visible or near-visible light photons) by the absorbed photons or particles. The number of photons produced is proportional to the energy of the absorbed primary photon or particle. The resultant light pulses are collected by a photo-cathode and can be counted to resolve the energy. Such scintillator configurations can include an electron photomultiplier, a silicon electron photomultiplier array (SiPM), an avalanche photodiode, or other detection means known in the art. Table 1 lists properties of several different possible scintillator materials. Any of the materials shown below or any other suitable material can be used.

TABLE 1

| | LaBr$_3$ | LaCl$_3$ | NaI(Tl) | CsI(Tl) | CsI(Na) | BGO | LYSO |
|---|---|---|---|---|---|---|---|
| Density (g/cm$^3$) | 5.29 | 3.86 | 3.67 | 4.51 | 4.51 | 7.13 | 7.10 |
| Light Output (ph/MeV) | 63,000 | 49,000 | 39,000 | 52,000 | 45,000 | 9000 | 32,000 |
| ΔE/E PMT | <3% | 3.5% | 7% | 6% | 7.5% | 10% | 7.1% |
| (FWHM) APD @662 keV | N/A | N/A | 3.8% | 4.9% | N/A | 8.3% | N/A |
| Peak λ (nm) | 380 | 350 430 | 310 fast 415 | 550 | 420 | 480 | 420 |
| Fast Decay (ns) | 25 | 25/213 | 620 fast 230 | 1000 | 630 | 300 | 41 |
| Hygroscopic | yes | yes | yes | slightly | yes | no | no |
| Cost (per cm$^3$) | $ 30 | $ 30 | $ 2 | $ 4.50 | $ 4.50 | $ 9 | $ 25 |
| Radiation length (cm) | N/A | N/A | 2.9 | 1.86 | 1.86 | 1.1 | 1.2 |

Figure 4A:
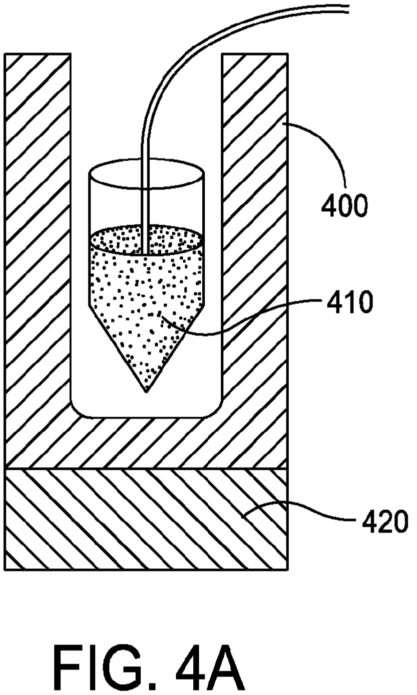
FIG. 4A is a side cross-sectional illustration of a scintillator with an annular cutout, in one aspect of the present disclosure.
Figure 4B:
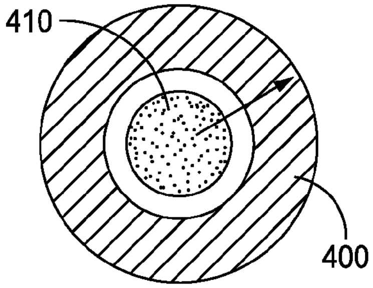
FIG. 4B is a top view of the scintillator of FIG. 4A.

FIGS. 4A and 4B are diagrams of a scintillator 400 with an annular cutout, in one aspect of the disclosure. FIG. 4A is a side sectional view and FIG. 4B is a top view. Such a scintillator can be configured as a single piece, an array, two halves bonded together, or any other suitable configuration. In the example shown, the scintillator 400 is cylindrical in shape with a side wall that surrounds the vial 410 and bottom. The top portion of the scintillator is open to allow the vial 410 to be positioned inside the cavity of the scintillator 410. The scintillator structure is sufficiently tall to ensure high solid angle coverage including when the microbeads 410 and injection material are being actively mixed. In some examples, the side wall of the scintillator 400 can be one and a half times as tall as the vial 410. In other examples, the side wall of the scintillator 400 can be about (+/−10%) twice as tall as the vial 410. In other examples, the side wall of the scintillator 400 can have other sizes relative to the height of the vial 410. As shown in FIG. 4A, a detector 420 can be included to detect light emitted from the scintillator 400. In this example, the detector 420 is positioned under a base of the scintillator 400. In other examples, the detector can be positioned in other locations. The detector signal is proportional to the amount of light generated by the scintillator 400. The detector signal can be used, in turn, to determine a radioactivity of the radioembolization material in the vial 410.

Figure 5A:
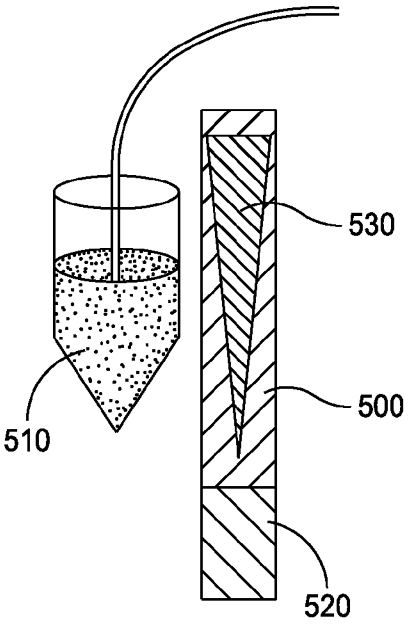
FIG. 5A is a side view of a scintillator in another aspect of the present disclosure.
Figure 5B:
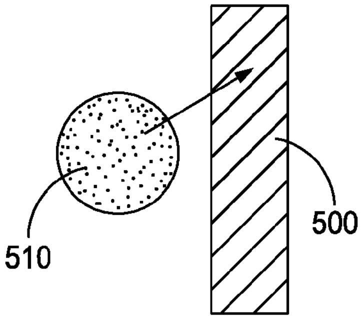
FIG. 5B is a top view of the scintillator of FIG. 5A.

FIGS. 5A and 5B are diagrams of a scintillator 500 and a detector 520 in another aspect of the disclosure. FIG. 5A is a side sectional view and FIG. 5B is a top view. This is an elongated scintillator 500 where the solid angle remains nearly the same when the microbeads 510 are being actively mixed. Because the detector 520 is shown as being positioned at a shallow angle with respect to the solution with the microbeads 510, detecting uniform light output is a possible concern. As shown in FIG. 5A, a uniformity device 530 can be included to make the light output from the scintillator 500 more uniform. For example, the uniformity device 530 can be a baffle, a reflector, an absorber, or any other suitable device.

In this example, the scintillator 500 is a panel of scintillator material positioned on one side of the vial 510. In other examples, similar panels of scintillator material can be positioned on two or more sides on the vial 510. Such panels of scintillator material can be joined together if desired. In such alternative examples, the detector 520 can be extended and positioned in communication with the scintillator materials to detect the light illuminated by the scintillator panels.

This disclosure is not intended to be limited to the specific geometries of scintillator and detectors shown in FIGS. 4-7, which are provided as exemplary embodiments. The radiation monitoring device of this disclosure can employ other configurations of scintillators and detectors.

Figure 6:
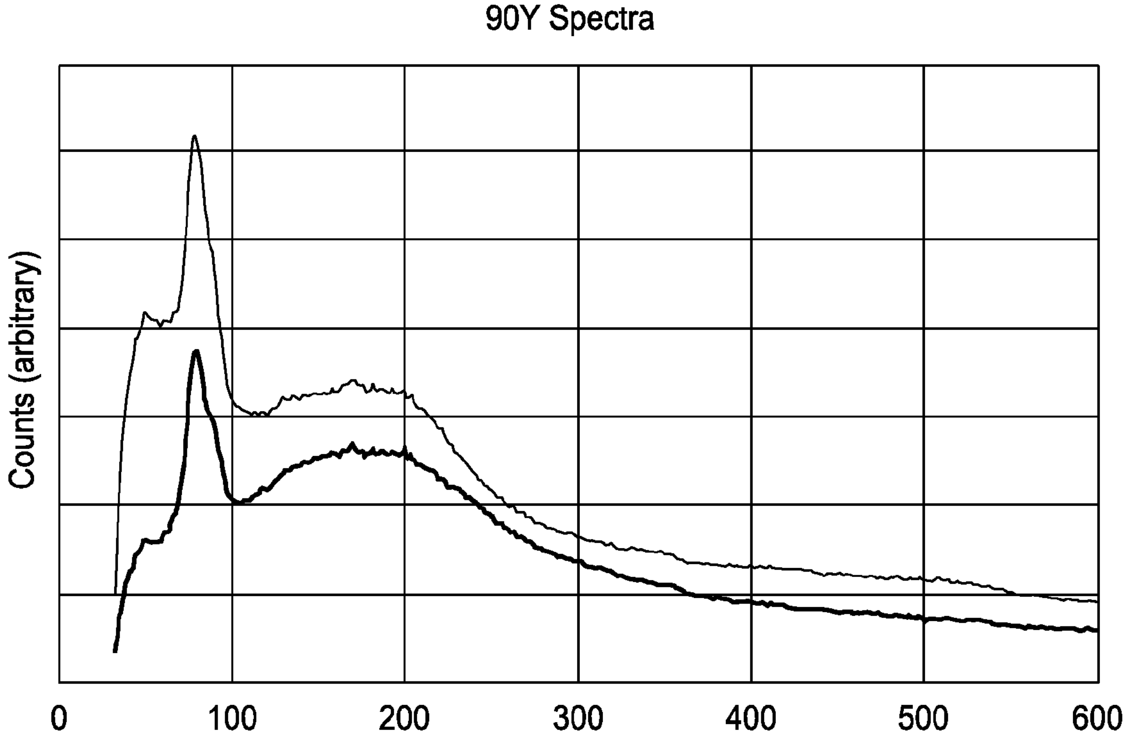
FIG. 6 is a graph of counts versus photon energy.

FIG. 6 is an example graph of counts versus photon energy (keV). The curves in FIG. 6 represent a distribution of energies that can be detected by a scintillator. As discussed above, the ratio of photons detected at different energies can be used to determine the age of the mixture by comparison with the known ratio of photons at different energies at the time the mixture was created/prepared, based on the known half-lives of the various isotypes present in the mixture.

Figure 7A:
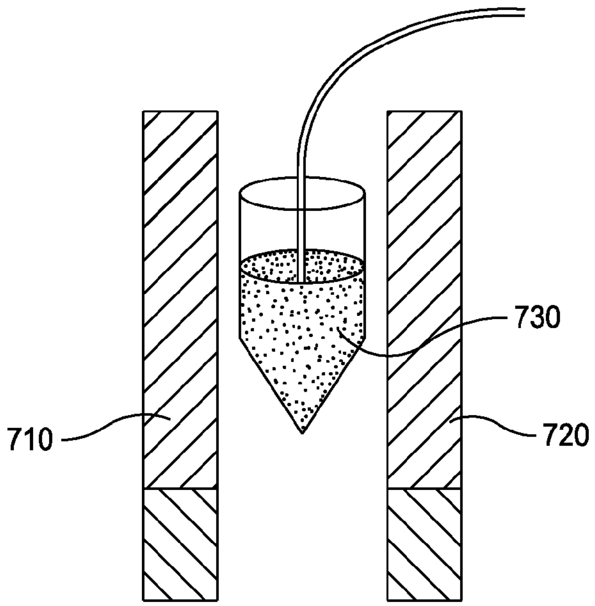
FIG. 7A is a side view of a scintillator in another aspect of the present disclosure.
Figure 7B:
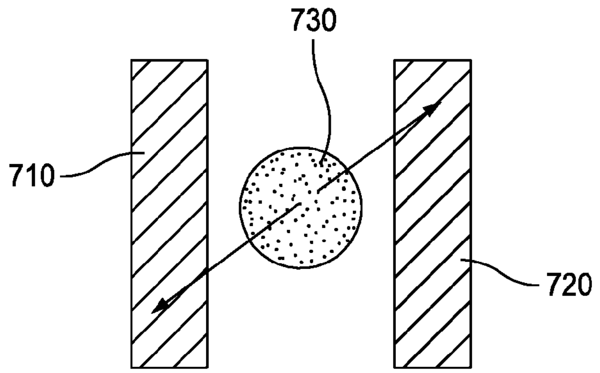
FIG. 7B is a top view of the scintillator of FIG. 7A.

FIGS. 7A and 7B are diagrams of a scintillator configuration in another aspect of the disclosure. FIG. 7A is a side sectional view and FIG. 7B is a top view. This configuration includes two scintillators 710 and 720. The first scintillator 710 can be positioned on a first side of the vial 730 and the second scintillator 720 can be positioned on a second side of the vial 730. The first scintillator 710 can be positioned on an opposite side of the vial 730 than the second scintillator 720. A height of each scintillator 710, 720 should be sufficiently tall to ensure high solid angle coverage including when the microbeads and injection material in vial 730 are being actively mixed. In some examples, the scintillators 710, 720 can be one and a half times as tall as the vial 730. In other examples, scintillators 710, 720 can be twice as tall as the vial 730. In other examples, scintillators 710, 720 can have other relative sizes relative to the height of the vial 730.

The scintillator configuration shown in FIGS. 7A, 7B can be used, for example, to measure radioembolization material that emits direct gamma rays such as HO-166 and Tc-m 99 materials. In other materials, an indirect gamma ray detection is used such as the detection of Bremsstrahlung gamma rays. Such Bremsstrahlung gamma rays are not directly emitted by other radioembolization materials (e.g., Y-90 materials). Instead, such Bremsstrahlung gamma rays are emitted when electrons emitted by the radioembolization materials strike other particles in the radioembolization materials such as the glass material of the microbeads. Thus, the radioactivity of the radioembolization material is indirectly measured.

The scintillator configuration shown in FIGS. 7A and 7B can be used to measure direct gamma ray emitters using a coincidence detection circuit. In such a method, the detector can detect when the scintillators are struck by opposing particles on opposite sides of the vial 730. Such a condition is illustrated in FIG. 7B. When the detector detects a condition in which two particles are emitted simultaneously (represented by the arrows) from the same source (e.g., a beta particle and a gamma ray) of vial 730. One particle can strike the first scintillator 710 and a second opposing particle can strike the second scintillator 720. The detector and coincidence detection circuit can determine and count the frequency of such occurrences. This, in turn, can be used to isolate the frequency of direct gamma ray emission from indirect gamma ray emission that is generated due to internal generation of energy in the vial 730. In this manner, the scintillator configuration of FIG. 7A can measure the radioactivity of a direct gamma ray radioembolization material.

The dosimeters and/or detectors of the present disclosure can be configured in different manners to measure and/or determine a radioactivity of the radioembolization materials using one or more different radioactivity measurement methods. Activity measurement mode and hardware options of the dosimeters and/or detectors can depend on the type of the particles/beads used for the embolization. Particles containing direct gamma-ray emitting isotopes, e.g. Ho-166, Tc-m 99, Cu-67, emit gamma rays in the energy range of 80-148 keV with a branching ratio of 10-100% of gamma-ray emission rate to total decay rate. In one example, the direct gamma-rays can be measured to determine a radioactivity of the radioembolization material.

One advantage of direct gamma-ray measurement or detection is that gamma rays of the energies described above can be detected using relatively small scintillating detectors. Alternatively, they can be detected using direct conversion detectors, such as, for example, CdTe, CZnTe, or Si.

Another advantage of direct gamma-ray measurement or detection is that single gamma-ray energy line or a few lines allows to use an energy window to suppress secondary gamma-rays emitted via bremsstrahlung of beta-particles (e.g. by Y-90). Since the bremsstrahlung x-rays have a broad spectrum and lower intensity, their background activity will not affect the measurement of activity through direct gamma-rays.

In another advantage of direct gamma-ray measurement or detection, the intensity of the emitted gamma rays is high due to high gamma-ray branching ratio. The high intensity corresponds to high count rate and higher accuracy of activity measurement due to Poisson Statistics.

In another advantage of direct gamma-ray measurement or detection, the activity measurement is independent of the mixing of the beads with the carrier liquid, because the gamma rays are emitted by the beads themselves.

In another advantage, the electronics of the dosimeter and/or detector is simpler compared to the electronics used in other detection/measurement dosimeters such as those used in 511 keV coincidence circuit detectors.

Consequently, in some devices and methods of the present disclosure, direct gamma-ray emitter radioembolization materials can be used. In such examples, the embolization particles should, therefore, contain the direct gamma-ray emitting isotopes. This can be done either by selecting the beta-emitter, which is also a gamma-ray emitter, e.g. Ho-166, by mixing two isotopes into one bead (e.g. Cu-67 for direct gamma rays and Y-90 for beta-), or by using a mixture of beads, some of them containing beta-isotope (e.g. Y-90) and others containing direct gamma ray emitting isotope (e.g. Cu-67).

In other examples, detectors and methods of the present disclosure can be used that determine a radioactivity of a radioembolization material by measuring and/or detecting indirect or secondary gamma rays. For particles containing beta-emitter, e.g. Y-90, the material will emit secondary bremsstrahlung gamma-rays. The dosimeters and/or detectors can be configured to measure the bremsstrahlung gamma-ray activity using thicker scintillators than are used to detect direct gamma-rays.

In one advantage of devices and methods that measure radioactivity using indirect or secondary gamma rays, there is no need for additional direct gamma-emitting isotopes for Y-90 beads embolization.

In another advantage, there is a higher gamma-ray rate in secondary or indirect gamma-rays than 511 keV beta+ annihilation rate. This higher rate corresponds to higher Poisson Statistics and correspondingly lower statistical errors.

In another advantage of devices and methods that measure radioactivity using indirect or secondary gamma rays, the electronics of such devices are simpler compared to the 511 keV coincidence detection electronics.

The measurement of indirect or secondary gamma-rays can depend on the mixing state of the radioembolization microbeads with the carrier liquid. When the beads are not actively mixed and resting packed at the bottom of the vial, the beta particles predominantly collide with other beads and emit bremsstrahlung in collisions with atoms of the beads. On the other hand, when the beads are actively mixed and distributed more evenly throughout the carrier liquid, the beta particles are colliding predominantly with the atoms of the carrier liquid. In this case, the bremsstrahlung emission probability is different. Therefore, the measured activity of the radioembolization material can be corrected based on the status of the mixing. This can be done using pre-defined calibration factors.

In other devices and methods, the radioactivity of the radioembolization material can be determined by using dosimeters and/or detectors that measure a 511 keV annihilation rate. Particles containing beta-emitter, e.g. Y-90, will also emit beta+ particles, which decay into pairs of gamma rays with the energy of 511 keV and traveling in exact opposite directions. These 511 keV pairs can be detected using a pair of the detectors (e.g. scintillators) and coincidence electronics to separate coincident events from the single events, which constitute the background.

It is an advantage of such devices and methods that are configured to measure the 511 keV annihilation rate that the detected rate is independent of the mixing state, because nearly all beta+ particles will annihilate into pairs of 511 keV regardless of the surrounding material.

In another advantage of devices and methods that are configured to measure the 511 keV annihilation rate, coincidence detection will help eliminate background due to bremsstrahlung. The energy measurement and the energy window around 511 keV will further suppress the background. With the combination of these two measures, the background can be nearly completely eliminated In another advantage, this method measures activity of Y-90, and does not require presence of additional isotopes.

Depending on the device and/or method used to measure and/or determine the radioactivity of radioembolization material, a statistical error can differ. The statistical errors will depend on the counted detected gamma-ray events "C". The relative error of the activity measurements is 1/sqrt (C). The detected activity depends on the solid angle of the detectors and the gamma-ray branching ratios.

Direct gamma-ray emitters: 1 (Tc-m 99), 0.1 (Ho-166)

Bremsstrahlung Y-90: 3e-2

Annihilation 511 keV Y-90: 3e-5

Below the statistical errors are estimated for the most difficult case of beta+ annihilation 511 keV gamma rays, which will produce the lowest count rate and the highest errors. The cases of bremsstrahlung (indirect or secondary gamma rays) and direct gamma ray emitters will produce lower errors. For the error estimation below, it is assumed:

the detector solid angle coverage of 30%; activity in the beginning of the procedures is 1 GBq; and activity at the end of the procedure is 10 MBq.

In the beginning of an example procedure, the activity is 511 keVis 1e9*3e-5 =3e4 Bq. The count rate is 3e4*0.3=1e4 Hz. When counting for 1 second the relative error is 1/sqrt (1e4)=0.01, which corresponds to the activity measurements error of 10 MBq. When counting for 10 seconds, the error can be reduced to 3 MBq. At the end of the procedure, the remaining activity in the vial can be assumed 10 MBq, which will produce the count rate of 1e2 Hz, producing in 1 second integration the error of 1 MBq.

To compare these errors with the injected activities, it is assumed that in the beginning of the procedure large volume lesions are embolized, and at the end of the procedure, smaller remaining lesions are treated. The target dose in the lesion is 120 Gy or higher. Assuming this dose, the following activities are expected to be injected (calculated based on Y-90 half-life and total dose deposited over several half-lives):

Large legion: 200 cm3: 500 MBq

Small lesion: 30 cm3: 70 MBq

Very small lesion (low limit): 1 cm3: 2 MBq

These target activities can be measured with acceptable errors using the 511 keV technique. The other proposed methods of measuring a radioactivity of the radioembolization material (i.e. direct gamma-ray, and indirect gamma-ray) will allow for more accurate measurements.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A device to measure radioactivity of a radioembolization material, the device comprising a dosimeter configured to measure the radioactivity of the radioembolization material in a vial contained in a vessel during a radioembolization procedure, wherein the dosimeter is positioned between an inside wall of the vessel and the vial.

2. The device of claim 1, further comprising the vessel and wherein:

the vessel is a container to receive the radioembolization material, and the dosimeter measures the radioactivity of the radioembolization material in the container while the radioembolization material is being administered to a patient.

3. The device of claim 1, wherein:

the vessel is a conduit, the dosimeter is positioned adjacent to the conduit during the radioembolization procedure, the dosimeter configured to measure the radioactivity of the radioembolization material as the radioembolization material moves through the conduit; and the device further comprises a flow meter that measures a flow velocity of the radioembolization material as the radioembolization material moves through the conduit.

4. The device of claim 1, configured to adjust delivery of the radioembolization material during the radioembolization procedure in dependence upon the measured radioactivity of the radioembolization material.

5. The device of claim 1, configured to determine a radioactive dose that is delivered to a patient during the radioembolization procedure.

6. The device of claim 1, wherein the radioembolization material includes multiple sources of radioactivity and the device is configured to determine an age of the radioembolization material in dependence upon different half-life times of the multiple sources of radioactivity.

7. The device of claim 1, wherein the radioembolization material comprises radioactive microspheres.

8. The device of claim 1, wherein the dosimeter includes a scintillator having a cylindrical shape with a side wall and a bottom to surround the vial.

9. The device of claim 8, wherein the side wall of the scintillator is about twice as tall as the vial.

10. The device of claim 1, wherein the dosimeter includes a scintillator having a planar shape and positioned on one side of the vial.

11. The device of claim 10, further including a uniformity device to make light output from the scintillator more uniform.

12. The device of claim 1, wherein the dosimeter includes a first scintillator positioned on a first side of the vial and a second scintillator positioned on a second side of the vial, and the second side is opposite to the first side.

13. The device of claim 1, wherein the radioactivity is displayed on a display.

14. A method to measure radioactivity of a radioembolization material administered into a patient's vasculature, the method comprising:

measuring an initial radioactivity and a subsequent radioactivity of the radioembolization material in a vial within a container using a dosimeter positioned between an inside wall of the container and the vial during a radioembolization treatment; and calculating a difference between an initial radioactivity of the radioembolization material in the vial prior to administration of the radioembolization material into the patient's vasculature and a subsequent radioactivity of the radioembolization material before ceasing administration of the radioembolization material into the patient's vasculature.

15. The method of claim 14 further comprising measuring a flow rate of the radioembolization material during administration of the radioembolization material into the patient's vasculature.

16. The method of claim 14, wherein measuring the initial radioactivity and the subsequent radioactivity of the radioembolization material in the vial is performed by detecting indirect or secondary gamma rays.

17. The method of claim 14, wherein measuring the initial radioactivity and the subsequent radioactivity of the radioembolization material in the vial is performed by detecting a 511 keV annihilation rate.

18. The method of claim 14, further comprising displaying the radioactivity of the radioembolization material in the vial and the difference between the initial radioactivity and the subsequent radioactivity of the radioembolization material on a display.

19. A method to measure radioactivity of a radioembolization material in a vial within a container and administered into a patient's vasculature, the method comprising:

measuring a radioactivity of the radioembolization material and a flow rate of the radioembolization material during administration of the radioembolization material into the patient's vasculature, wherein the radioactivity is measured using a dosimeter positioned between an inside wall of the container and the vial; and calculating a rate with which the radioactivity is being administered to the patient.

20. The method of claim 19 wherein the measuring the radioactivity of the radioembolization material and the flow rate of the radioembolization material is performed as the radioembolization material moves through a conduit.

* * * * *